United States Patent [19]

Jennings

[11] Patent Number: Plant 5,697

[45] Date of Patent: Mar. 25, 1986

[54] TUMMELBERRY

[75] Inventor: Derek L. Jennings, Dundee, Scotland

[73] Assignee: National Seed Development Organisation Limited, Newton, England

[21] Appl. No.: 617,392

[22] Filed: Jun. 5, 1984

[51] Int. Cl.[4] ..... A01H 5/03

[52] U.S. Cl. ..... Plt./46

[58] Field of Search ..... Plt./46

*Primary Examiner*—Robert E. Bagwill

*Attorney, Agent, or Firm*—Burns, Doane, Swecker & Mathis

[57] ABSTRACT

The invention relates to a new and distinct hybrid Rubus variety which has been named the Tummelberry. The subject variety was formed by crossing seedling 69102/18, an unnamed hybrid bred at the Scottish Crop Research Institute, with the Tayberry as pollen parent. The variety resembles the Tayberry in some respects, but differs from it in the flavor, size, shape and color of its fruit, in the season of ripening and in the intensity of red pigments present in the stems and leaves.

6 Drawing Figures

SUMMARY OF THE INVENTION

The original plant was selected from a family of seedlings resulting from a cross made in 1973 at the Scottish Crop Research Institute (SCRI), Dundee, United Kingdom, between the Tayberry and seedling 69102/18. The latter was bred at the SCRI and served as the maternal parent. The Tayberry is a blackberry-raspberry hybrid also bred at the SCRI which is the subject of U.S. Plant Pat. No. 4,424.

The present variety resembles the Tayberry in some respects, but differs from it in the flavor, color, size and shape of its fruit, in the season of ripening, and in the intensity of the red plant pigments present in the stems and leaves.

The performance of the new variety has been evaluated in trials at the Scottish Crop Research Institute; the National Fruit Trials at Faversham, England; and elsewhere in the United Kingdom. Repeated asexual propagations have demonstrated that the characteristics of the new variety are stable and are transmitted without change through succeeding propagations. The variety may be reproduced with ease by the use of leaf-bud cuttings, rooted tips, suckers produced in a spawn-bed, or tissue culture.

The new variety was initially designated the Clydeberry, and subsequently has been renamed the Tummelberry.

BRIEF DESCRIPTION OF THE PHOTOGRAPHS

The accompanying photographs show typical specimens of the new variety in color as nearly true as is reasonably possible to make the same in a color illustration of this character. In each instance the photographs were made at the Scottish Crop Research Institute, Dundee, United Kingdom.

DETAILED DESCRIPTION

Figure 1:
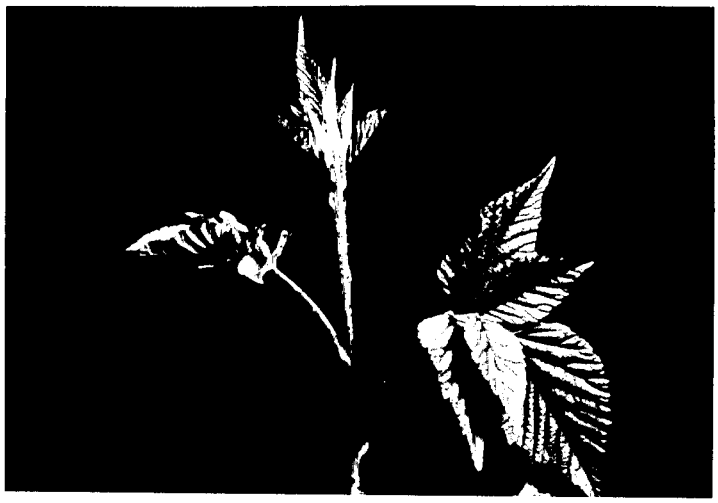
FIG. 1 is a young shoot tip of Tummelberry plant photographed in June, 1983.
Figure 2:
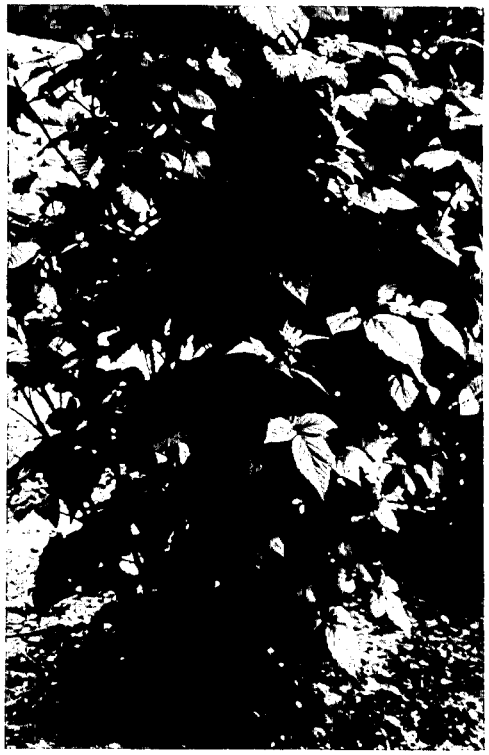
FIG. 2 is a mature Tummelberry plant photographed in June, 1983, which shows the erect growth habit of new stems during the early part of the season.
Figure 4:
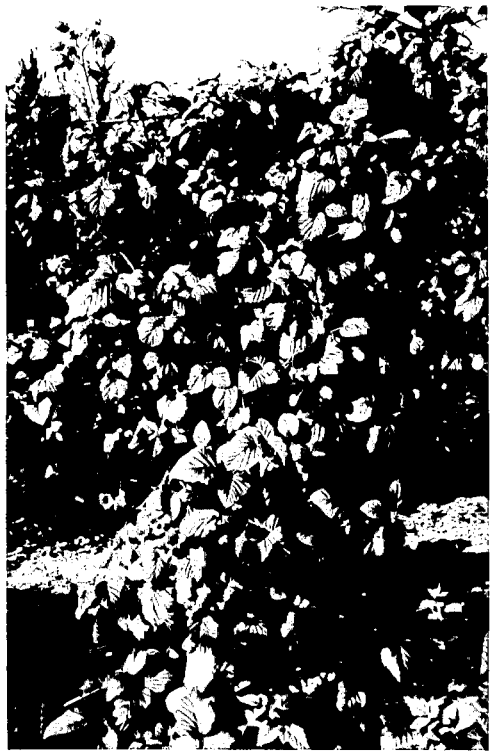
FIG. 4 is a closer view of a single Tummelberry plant from the row shown in FIG. 3.
Figure 3:
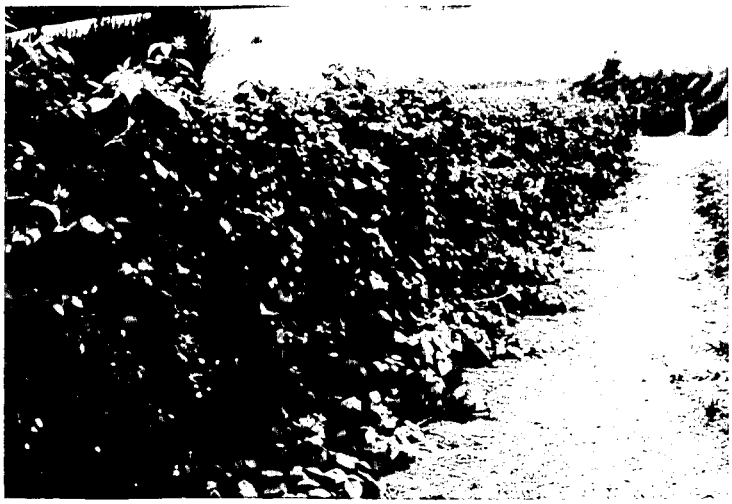
FIG. 3 is a row of mature Tummelberry plants photographed in August, 1983, at harvest time.
Figure 5:
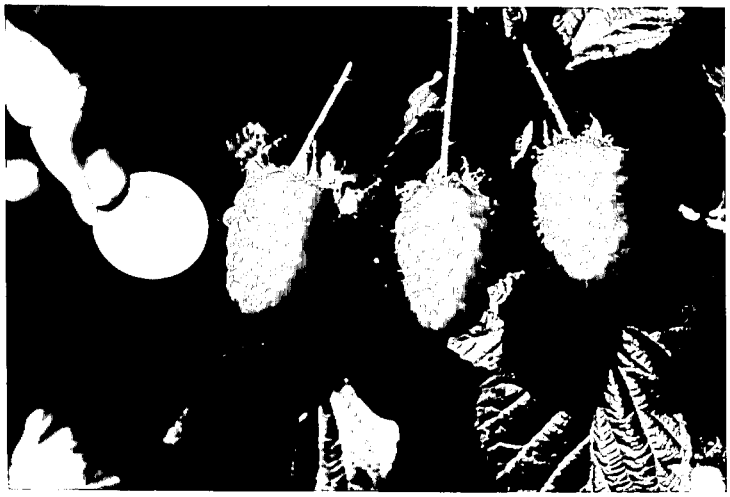
FIG. 5 is a close view of three Tummelberry fruits borne by a plant of the row shown in FIG. 3 while adjacent to a 10 pence coin.
Figure 6:
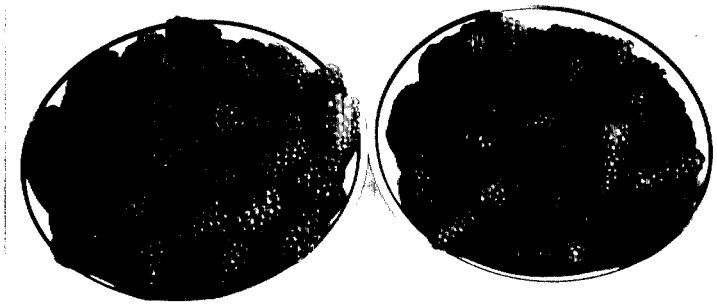
FIG. 6 shows a dish of Tummelberry fruit on the left and a dish of Tayberry fruit on the right, photographed in July, 1980, to contrast the short conical shape and more red color of the Tummelberry with the long conical shape and red-purple color of the Tayberry.

The following is a detailed description of the new variety as observed at the Scottish Crop Research Institute, Dundee, United Kingdom. Color terminology employed is to be accorded its ordinary dictionary significance. As will be apparent to those skilled in the horticultural science, the colors of the leaves and stems vary with the stage of growth and are useful only for general guidance. Simiarly, the fruit color varies with the stage of ripeness.

DESCRIPTION OF ONE YEAR OLD VEGETATIVE SHOOTS

The new variety exhibits vigorous, sturdy shoots, which are erect during the early part of the season but become semi-erect or prostrate as growth proceeds. The spines are dense, elliptical in shape, and highly pigmented at their base and tip. The leaves are a medium green and generally lack red pigmentation around the margins of older leaves and in the petioles. The substantial lack of pigmentation is a point of difference from the Tayberry (U.S. Plant Pat. No. 4,424). The leaflets are usually five in number and have a distinct relief between the veins. Suckering in the true botanical sense does not occur, but established plants commonly produce from approximately 5 to 9 replacement canes from rootstock buds.

General habit:

*Strength of growth.*—Vigorous, sturdy shoots produced in moderate to high numbers.

*Habit of growth.*—Erect in early part of season, becoming semi-erect or prostrate by the end of the season.

*Coloring.*—Medium green with anthocyanin pigments absent or inconspicuous.

*Spines.*—Only moderately sized, dense, elliptical at their base and intensely pigmented (red in coloration) at base and tip. Triangulate and with short sharp tip.

*Hairiness.*—Absent or weak.

*Bloom.*—Weak.

*Leaflets.*—Usually five and touching each other.

*Leaf color.*—Medium to dark green, red pigments usually are absent.

*Petiole.*—Medium length, red pigments usually are absent.

*Lateral leaflets.*—No stalklets are present.

*Leaf veins.*—Medium to strong relief between veins.

DESCRIPTION OF DORMANT CANES

The new variety exhibits dormant canes which typically are 9 to 10 feet long, densely spined, semi-erect or prostrate, and of medium diameter. The purple coloring of the upper and lower parts is weak which is a point of difference from the Tayberry (U.S. Plant Pat. No. 4,424). The Tayberry commonly exhibits highly pigmented canes.

DESCRIPTION OF FRUITING LATERALS, FLOWERS AND FRUIT

White flowers and later fruits are well presented on stiff fruiting laterials, which are spiny and of about one foot length. The fruits are typically red to deep red and change to reddish-purple when fully ripe. They are large and short conical in shape. The fruits of the present variety are shorter and more red in color than those of the Tayberry (U.S. Plant Pat. No. 4,424). They have a slightly glossy appearance with only slight downiness. The flavor has a pleasant sharpness with little of the aromatic flavor characteristic of the Tayberry. The fruits separate from the plant with the plug remaining attached. Ripening commences about a week after the Tayberry and continues for about a week after the Tayberry.

General description:

*Fruiting laterals.*—Usually about one foot long.

*Flower.*—Medium size with prominent receptacle.

*Pedicel.*—Green, medium in length and lacking red pigment.

*Fruit.*—Large, deep red changing to red-purple when over-ripe, short conical shape with high drupelet number. The fruit weight commonly is approximately 4 to 5 grams during a wet season and less during a dry season. Fruit dimensions commonly range from approximately 26 to 35 mm. (e.g., 30 mm.) by approximately 19 to 22 mm. (e.g. 21 mm.). There are typically from approximately 5 to 7 fruits per lateral. The fruit is similar to the Tayberry with respect to juiciness.

*Fruit quality.*—Medium firm, slightly glossy, pleasantly sharp and highly flavored.

*Plug.*—Large, short conical, separates with the fruit when picked.

*Season of ripening.*—Equal to a late-season raspberry and one week later than the Tayberry. Ripening extends over a long period.

*Yield.*—The fruit yield per plant is influenced considerably by plant spacing and rainfall. For plants spaced three feet apart in rows nine feet apart a typical yield is 3 kg. per plant during a dry season.

*Disease and pest resistance.*—Is susceptible to cane spot (*Elsinoe veneta*) and leaf and bud mite (*Phyllocoptes gracilis*).

*Storage capability.*—The storage capability of the fruit is comparable to that of the Loganberry. The fruit stores well when deep frozen.

I claim:

1. A new and distinct variety of hybrid Rubus substantially as herein shown and described.

* * * * *